United States Patent
Hagiwara

(10) Patent No.: US 10,083,526 B2
(45) Date of Patent: Sep. 25, 2018

(54) RADIATION TOMOGRAPHIC IMAGING METHOD, APPARATUS, AND PROGRAM

(71) Applicant: General Electric Company, Schenectady, NY (US)

(72) Inventor: Akira Hagiwara, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 27 days.

(21) Appl. No.: 15/273,437

(22) Filed: Sep. 22, 2016

(65) Prior Publication Data

US 2017/0091962 A1    Mar. 30, 2017

(30) Foreign Application Priority Data

Sep. 24, 2015   (JP) ................................. 2015-187187

(51) Int. Cl.
*G06K 9/00* (2006.01)
*G06T 11/00* (2006.01)
(Continued)

(52) U.S. Cl.
CPC ............ *G06T 11/003* (2013.01); *A61B 6/032* (2013.01); *A61B 6/503* (2013.01); *A61B 6/5264* (2013.01);
(Continued)

(58) Field of Classification Search
CPC ......... A61B 6/032; A61B 6/027; A61B 6/503; A61B 6/583; A61B 6/00; A61B 6/4035;
(Continued)

(56) References Cited

U.S. PATENT DOCUMENTS

| 5,825,842 | A | * | 10/1998 | Taguchi | ................. | A61B 6/032 378/15 |
| 5,862,198 | A | * | 1/1999 | Samarasekera | ........ | A61B 6/032 378/4 |
| 6,404,844 | B1 | * | 6/2002 | Horiuchi | ................ | A61B 6/032 378/16 |
| 6,466,640 | B1 | * | 10/2002 | Taguchi | ................. | A61B 6/032 378/15 |

(Continued)

OTHER PUBLICATIONS

Unofficial English Translation of Japanese Office Action issued in connection with corresponding JP Application No. 2015-187187 dated Aug. 8, 2017.

*Primary Examiner* — Aklilu Woldemariam
(74) *Attorney, Agent, or Firm* — Fletcher Yoder, P.C.

(57) ABSTRACT

To detect motion in a subject, particularly, local rapid motion, during radiation tomographic imaging. There is provided a radiation tomographic imaging method causing a computer to execute: a controlling step of controlling a data collection subsystem comprising a multi-slice detector to collect data by performing a helical scan on a subject; a first reconstructing step of reconstructing a plurality of tomographic images at an identical slice position and at different times using data obtained by applying weighting to the collected data according to the slice position, the reconstruction being performed for a plurality of slice positions; a fragmenting step of fragmenting each of the plurality of tomographic images at each of the plurality of slice positions into a respective plurality of local-region images; and a difference identifying step of, for each combination of a plurality of local-region images at the same position and at different times, identifying a difference among local-region images in the combination.

17 Claims, 14 Drawing Sheets

(51) Int. Cl.
*A61B 6/03* (2006.01)
*A61B 6/00* (2006.01)
*G06T 7/00* (2017.01)
*G06T 7/20* (2017.01)

(52) U.S. Cl.
CPC .............. *G06T 7/0012* (2013.01); *G06T 7/20* (2013.01); *G06K 9/00* (2013.01); *G06T 2207/10081* (2013.01); *G06T 2207/30048* (2013.01)

(58) Field of Classification Search
CPC ....... A61B 6/405; A61B 6/461; A61B 6/5288; A61B 6/5264; A61B 6/037; A61B 6/484; A61B 6/508; A61B 6/0457; A61B 6/563; A61B 6/587; A61B 6/4028; A61B 6/488; A61B 6/542; A61B 6/03; A61B 6/0407; A61B 6/504; A61B 6/502; A61B 6/4085; A61B 6/541; A61B 6/481; A61B 6/507; G01N 2223/419; G01N 2223/612; G01N 23/043; G01N 23/046; G01N 2223/61; G06T 11/006; G06T 2207/10081; G06T 2211/424; G06T 2211/432; G06T 2211/436; G06T 7/0012; G06T 15/08; G06T 11/005; G06T 11/008; G06T 17/10; G06T 2200/04; G06T 2207/30096; G06T 5/002; G06T 11/00; G06T 2207/20012; G01T 1/1644
USPC ..... 382/128, 131, 154, 312; 378/4, 5, 15, 16
See application file for complete search history.

(56) References Cited

U.S. PATENT DOCUMENTS

| | | | |
|---|---|---|---|
| 6,522,712 B1* | 2/2003 | Yavuz | G06T 11/005 378/4 |
| 2003/0123614 A1* | 7/2003 | Silver | G06T 11/005 378/146 |
| 2004/0252870 A1* | 12/2004 | Reeves | G06T 7/0012 382/128 |
| 2005/0047541 A1* | 3/2005 | Tsuyuki | A61B 6/00 378/4 |
| 2005/0123092 A1* | 6/2005 | Mistretta | A61B 6/032 378/23 |
| 2005/0152588 A1* | 7/2005 | Yoshida | G06T 7/0012 382/128 |
| 2005/0175143 A1* | 8/2005 | Miyazaki | A61B 6/032 378/19 |
| 2007/0036418 A1* | 2/2007 | Pan | A61B 6/5288 382/131 |
| 2007/0172104 A1* | 7/2007 | Nishide | A61B 6/032 382/131 |
| 2008/0144764 A1* | 6/2008 | Nishide | A61B 6/4035 378/5 |
| 2008/0152075 A1* | 6/2008 | Paliwal | A61B 6/032 378/16 |
| 2009/0022375 A1* | 1/2009 | Fidrich | G06K 9/6206 382/128 |
| 2009/0175562 A1* | 7/2009 | Pan | A61B 6/032 382/312 |
| 2011/0052027 A1* | 3/2011 | Noshi | A61B 6/032 382/131 |
| 2011/0069810 A1* | 3/2011 | Kondo | A61B 6/032 378/15 |
| 2017/0091962 A1* | 3/2017 | Hagiwara | A61B 6/032 |

* cited by examiner

FIG. 6

| Helical pitch HP | Rotation speed V of gantry (sec/rot) | | |
|---|---|---|---|
| | 1.0 | 0.7 | 0.4 |
| 0.9 | 556 (msec) | 389 (msec) | 156 (msec) |
| 1.375 | 114 (msec) | 80 (msec) | 32 (msec) |
| 0.1531 | – | – | – |

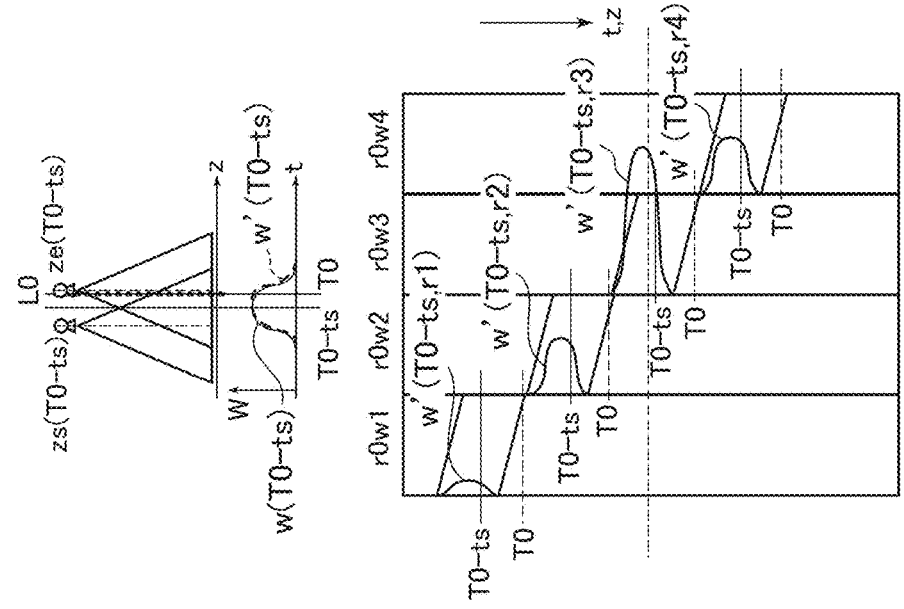
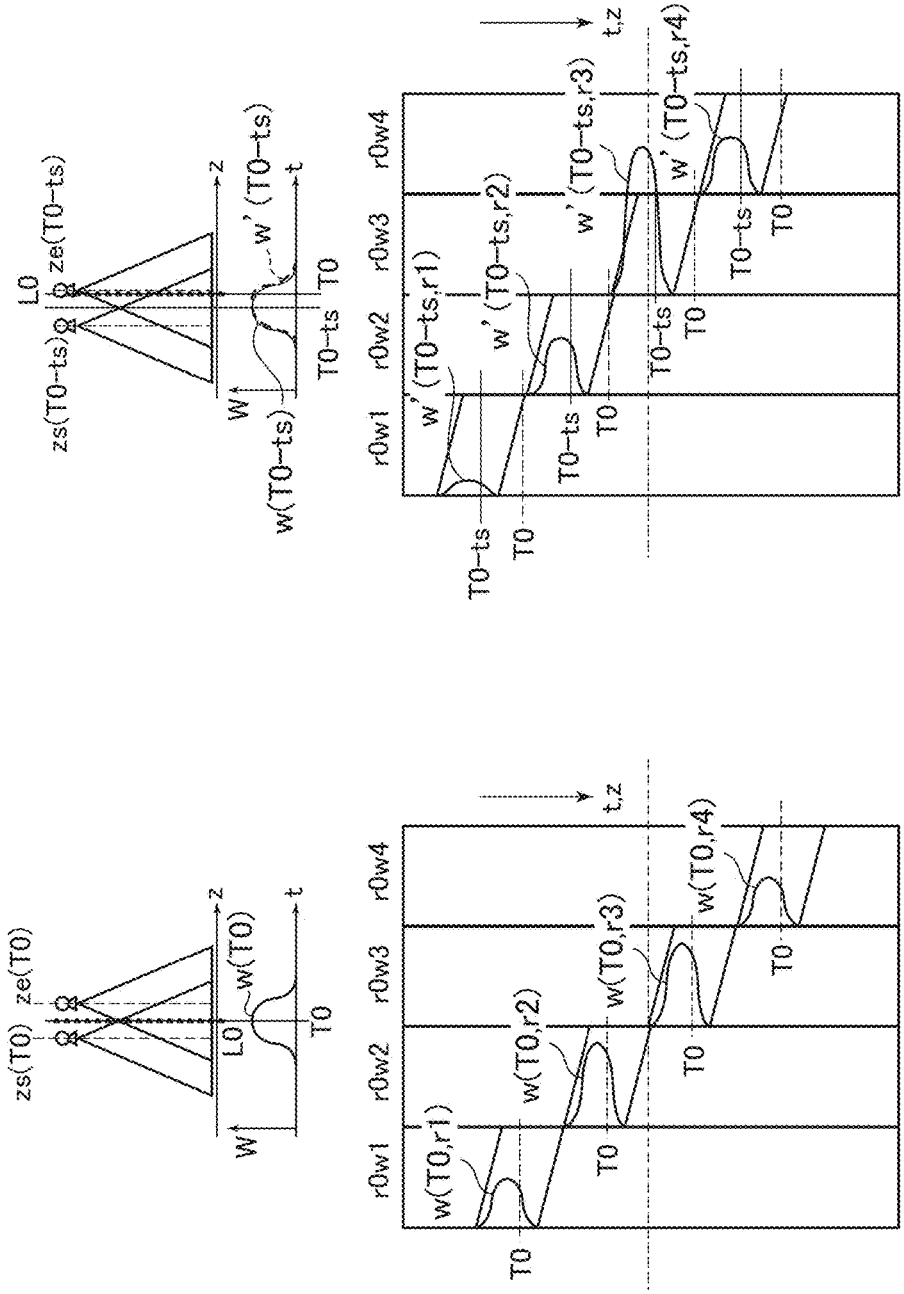
FIG. 10A
FIG. 10B

RADIATION TOMOGRAPHIC IMAGING METHOD, APPARATUS, AND PROGRAM

CROSS-REFERENCE TO RELATED APPLICATIONS

This application claims priority of Japanese Priority Application No. 2015-187187, entitled "RADIATION TOMOGRAPHIC IMAGING METHOD AND APPARATUS, AND PROGRAM", filed on Sep. 24, 2015 and listing Akira Hagiwara as sole inventor, which is herein incorporated by reference in its entirety for all purposes.

FIELD OF THE INVENTION

The present invention relates to a technique of detecting motion in a subject in radiation tomographic imaging.

BACKGROUND

In radiation tomographic imaging, motion in a subject during imaging may give rise to inconsistencies in collected data and generate artifacts in a tomographic image, causing a detrimental effect on diagnosis.

Accordingly, the subject is generally instructed not to move during imaging. Slow motion may be corrected to some degree because of a property of helical correction that a specific time is unevenly emphasized

SUMMARY OF THE INVENTION

Problem to be Solved by the Invention

On the other hand, peristaltic motion of intestines or movement of bubbles and/or liquid within the intestinal tract are very rapid motions and incontrollable. That is, artifacts resulting from such motion are very difficult to prevent. Should such artifacts be generated, re-imaging is often necessitated.

Artifacts caused by intestinal motion, etc., however, occur locally, so that they are difficult to find. Thus, sometimes an operator finishes imaging without realizing artifacts during an image check immediately after the imaging, but he/she finds them afterwards and is obliged to perform re-imaging.

Under such circumstances, there is a need for a technique capable of detecting motion, particularly, local rapid motion, in a subject during radiation tomographic imaging.

In its first aspect, the invention provides a radiation tomographic imaging method causing a computer to execute:

a controlling step of controlling a data collection subsystem comprising a multi-slice detector to collect data for a subject by performing a helical scan;

a first reconstructing step of reconstructing a plurality of tomographic images at an identical slice position and at different times using data obtained by applying weighting to said collected data according to said slice position, said reconstruction being performed for a plurality of slice positions;

a fragmenting step of fragmenting each of said plurality of tomographic images at each of said plurality of slice positions into a respective plurality of local-region images; and a difference identifying step of, for each combination of a plurality of local-region images at the same position and at different times, identifying a difference among local-region images in said combination.

In its second aspect, the invention provides the radiation tomographic imaging method in the first aspect above, comprising: a notifying step of, when a difference among local-region images in any said combination exceeds a specified level, notifying the fact.

In its third aspect, the invention provides the radiation tomographic imaging method in the first or second aspect above, wherein: said first reconstructing step applies said weighting using a weight function that has a relatively small weight for a region with a relatively large cone angle of a radiation path and a relatively large weight for a region with a relatively small cone angle of the radiation path, and in which a middle of the weight is coincident with a time of collection of data corresponding to a slice position for which image reconstruction is applied.

In its fourth aspect, the invention provides the radiation tomographic imaging method in the third aspect above, wherein: said first reconstructing step applies said weighting using a weight function tracing such a profile that a half width is equal between temporally backward and forward sides and a peak value is higher on a side closer to the time of collection of data corresponding to the slice position.

In its fifth aspect, the invention provides the radiation tomographic imaging method in any one of the first through fourth aspects above, comprising: an acquiring step of acquiring, when a difference among local-region images in any said combination exceeds a specified level, based on a difference among local-region images in said combination at the same position for two or more slice positions close to a specific slice position corresponding to said combination, a temporal change of an amount of motion of a body part at said specific slice position and at said same position.

In its sixth aspect, the invention provides the radiation tomographic imaging method in the fifth aspect above, comprising: an image identifying step of identifying a tomographic image at a time when the amount of motion of said body part is relatively small based on said temporal change.

In its seventh aspect, the invention provides the radiation tomographic imaging method in any one of the first through sixth aspects above, comprising: a presenting step of presenting, when a difference among local-region images in any said combination exceeds a specified level, imaging conditions for re-scanning a range including the specific slice position corresponding to said combination.

In its eighth aspect, the invention provides the radiation tomographic imaging method in any one of the first through seventh aspects above, comprising: a second reconstructing step of reconstructing a tomographic image by adding data acquired by said re-scan together with data acquired before said re-scan.

In its ninth aspect, the invention provides the radiation tomographic imaging method in any one of the first through eighth aspects above, wherein: said fragmenting step performs fragmentation into images each having a width approximating to a diameter of an intestinal tract as said local-region images.

In its tenth aspect, the invention provides a radiation tomographic imaging apparatus comprising:

controlling means for controlling a data collection subsystem comprising a multi-slice detector to collect data for a subject by performing a helical scan;

first reconstructing means for reconstructing a plurality of tomographic images at an identical slice position and at different times using data obtained by applying weighting to said collected data according to said slice position, said reconstruction being performed for a plurality of slice positions;

fragmenting means for fragmenting each of said plurality of tomographic images at each of said plurality of slice positions into a respective plurality of local-region images; and difference identifying means for, for each combination of a plurality of local-region images at the same position and at different times, identifying a difference among local-region images in said combination.

In its eleventh aspect, the invention provides the radiation tomographic imaging apparatus in the tenth aspect above, comprising: notifying means for, when a difference among local-region images in any said combination exceeds a specified level, notifying the fact.

In its twelfth aspect, the invention provides the radiation tomographic imaging apparatus in the tenth or eleventh aspect above, wherein: said first reconstructing means applies said weighting using a weight function that has a relatively small weight for a region with a relatively large cone angle of a radiation path and a relatively large weight for a region with a relatively small cone angle of the radiation path, and in which a middle of the weight is coincident with a time of collection of data corresponding to a slice position for which image reconstruction is applied.

In its thirteenth aspect, the invention provides the radiation tomographic imaging apparatus in the twelfth aspect above, wherein: said first reconstructing means applies said weighting using a weight function tracing such a profile that a half width is equal between temporally backward and forward sides and a peak value is higher on a side closer to the time of collection of data corresponding to the slice position for which image reconstruction is applied.

In its fourteenth aspect, the invention provides the radiation tomographic imaging apparatus in any one of the ninth through thirteenth aspects above, comprising: acquiring means for acquiring, when a difference among local-region images in any said combination exceeds a specified level, based on a difference among local-region images in said combination at the same position for two or more slice positions close to a specific slice position corresponding to said combination, a temporal change of an amount of motion of a body part at said specific slice position and at said same position.

In its fifteenth aspect, the invention provides the radiation tomographic imaging apparatus in the fourteenth aspect above, comprising: image identifying means for identifying a tomographic image at a time when the amount of motion of said body part is relatively small based on said temporal change.

In its sixteenth aspect, the invention provides the radiation tomographic imaging apparatus in any one of the tenth through fifteenth aspects above, comprising: presenting means for presenting, when a difference among local-region images in any said combination exceeds a specified level, imaging conditions for re-scanning a range including the specific slice position corresponding to said combination.

In its seventeenth aspect, the invention provides the radiation tomographic imaging apparatus in any one of the tenth through sixteenth aspects above, comprising: second reconstructing means for reconstructing a tomographic image by adding data acquired by said re-scan together with data acquired before said re-scan.

In its eighteenth aspect, the invention provides the radiation tomographic imaging apparatus in any one of the tenth through seventeenth aspects above, wherein: said fragmenting means performs fragmentation into images each having a width approximating to a diameter of an intestinal tract as said local-region images.

In its nineteenth aspect, the invention provides the radiation tomographic imaging apparatus in any one of the tenth through eighteenth aspects above, wherein:

the local-region images in said combination comprise first, second and third local-region images at mutually different times, and the difference among local-region images in said combination is a feature quantity using a differential between said first and second local-region images, and a differential between said second and third local-region images.

In its twentieth aspect, the invention provides a program for causing a computer to function as the means in the radiation tomographic imaging apparatus in any one of the tenth through nineteenth aspects above.

Effect of the Invention

According to the invention in the aspects described above, a plurality of images at different times are reconstructed at each slice position based on data obtained by a radiation-based helical scan, the images are each fragmented, and a difference is identified among local regions; therefore, motion in a subject, particularly, local rapid motion such as motion of the intestinal tract, during X-ray tomographic imaging may be detected based on the differences.

BRIEF DESCRIPTION OF THE DRAWINGS

FIG. 6 chart showing roughly estimated amounts of the time shift.

FIG. 10A A diagram showing a case of an X-ray CT apparatus comprising a four-row detector in another example of modification of the shape of the weight function corresponding to a case of a general helical scan without a time shift, wherein each row independently has a weight function.

FIG. 10B A diagram showing a case of an X-ray CT apparatus comprising a four-row detector in another example of modification of the shape of the weight function corresponding to a case of a general helical scan with a time shift.

MODES FOR CARRYING OUT THE INVENTION

Now an embodiment of the invention will be described hereinbelow. It should be noted that the invention is not hereby limited.

Figure 1:
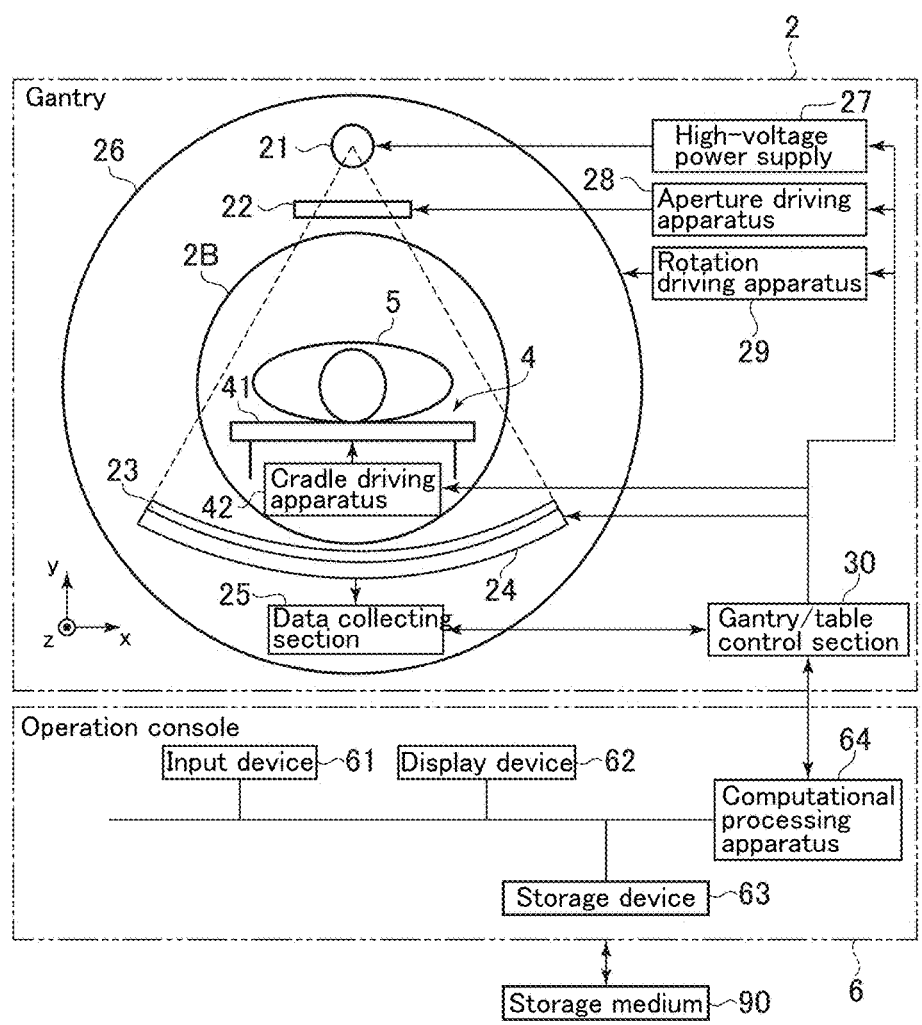
FIG. 1 A diagram schematically showing a hardware configuration of an X-ray CT apparatus in accordance with an embodiment of the present invention.

FIG. 1 is a diagram schematically showing a hardware configuration of an X-ray CT apparatus (X-ray Computed Tomography system) in accordance with the present embodiment.

As shown in FIG. 1, the X-ray CT apparatus 1 comprises a gantry 2, an imaging table 4, and an operation console 6.

The gantry 2 has an X-ray tube 21, an aperture 22, a collimator device 23, an X-ray detector 24, a data collecting section (data acquisition system) 25, a rotating section 26, a high-voltage power source 27, an aperture driving apparatus 28, a rotation driving apparatus 29, and a gantry/table control section 30.

The X-ray tube 21 and X-ray detector 24 are disposed to face each other across a bore 2B.

The aperture 22 is disposed between the X-ray tube 21 and bore 2B. It shapes X-rays emitted from the X-ray tube 21 at its X-ray focus toward the X-ray detector 24 into a fan beam or a cone beam.

The collimator device 23 is disposed between the bore 2B and X-ray detector 24. The collimator device 23 removes scatter rays that would otherwise enter the X-ray detector 24.

The X-ray detector 24 has a plurality of X-ray detector elements two-dimensionally arranged in a direction of the span and a direction of the thickness of the fan-shaped X-ray beam emitted from the X-ray tube 21. As used herein, the span direction will be referred to as channel direction, and the thickness direction as row direction. Each respective X-ray detector element detects X-rays passing through a subject 5 laid in the bore 2B, and outputs an electric signal depending upon the intensity thereof. The subject 5 is an animate being, such as, for example, a human or an animal.

The data collecting section 25 receives the electric signal output from each X-ray detector element in the X-ray detector 24, and converts it into X-ray data for collection.

The rotating section 26 is rotatably supported around the bore 2B. The rotating section 26 has the X-ray tube 21, aperture 22, collimator device 23, X-ray detector 24, and data collecting section 25 mounted thereon.

The imaging table 4 has a cradle 41 and a cradle driving apparatus 42. The subject 5 is laid on the cradle 41. The cradle driving apparatus 42 moves the cradle 41 into/out of the bore 2B, i.e., an imaging volume, in the gantry 2.

The high-voltage power source 27 supplies high voltage and current to the X-ray tube 21.

The aperture driving apparatus 28 drives the aperture 22 and modifies the shape of its opening.

The rotation driving apparatus 29 rotationally drives the rotating section 26.

The gantry/table control section 30 controls several apparatuses and sections in the gantry 2, the imaging table 4, and the like.

The operation console 6 accepts several kinds of operation from an operator. The operation console 6 has an input device 61, a display device 62, a storage device 63, and a computational processing apparatus 64. In the present embodiment, the operation console 6 is constructed from a computer.

As shown in FIG. 1, a direction of the body axis of the subject 5, i.e., a direction of transportation of the subject 5 by the imaging table 4, will be referred to herein as z-direction. Moreover, a vertical direction will be referred to as y-direction, and a horizontal direction orthogonal to the y- and z-directions as x-direction.

Next, a function of the X-ray CT apparatus in accordance with the present embodiment will be described. The X-ray CT apparatus in accordance with the present embodiment has a function of detecting motion in a subject, particularly, local rapid motion such as peristaltic motion of intestines or movement of bubbles and/or liquid within the intestinal tract, during imaging from data obtained by a scan, notifying the fact, and recommending consideration of re-imaging.

Next, the concept of a method of detecting motion in a subject during imaging and a method of handling after the detection according to the present proposal will be described in detail.

Generally, in helical image reconstruction, time and position are in one-to-one correspondence.

Figure 2:
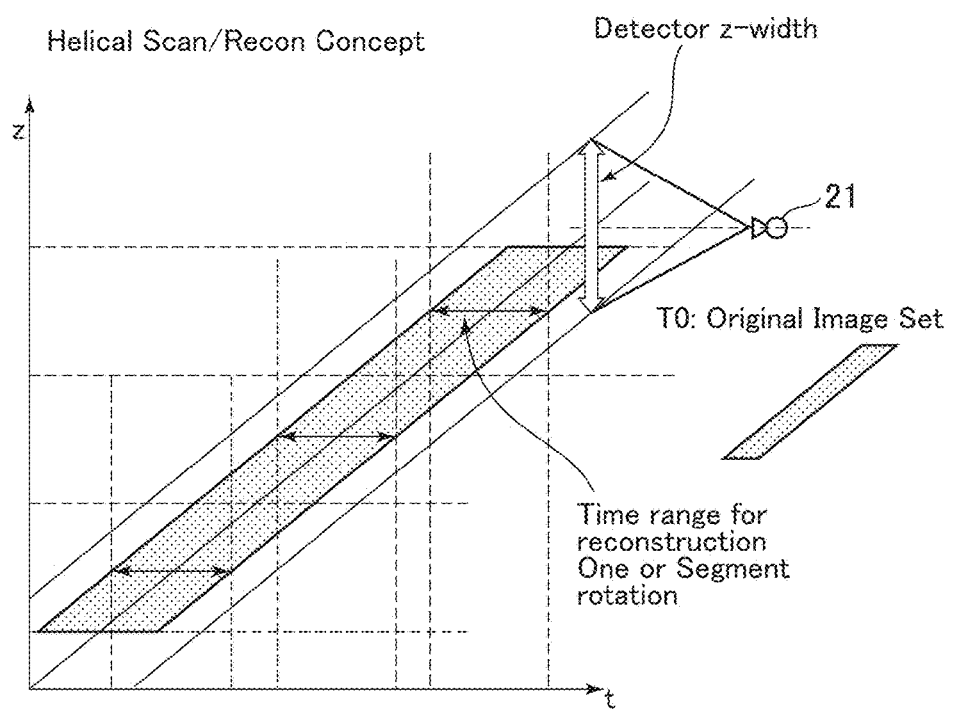
FIG. 2 A diagram showing a relationship between time and position during general imaging according to a helical scan.

FIG. 2 shows a relationship between time t and position z during imaging by a general helical scan. Because of helical imaging, the position of the X-ray detector changes with the lapse of time in one-to-one correspondence. Since the position of image production is always laid in the center of the range of movement of the detector around a specific time T0, the time and image position are in one-to-one correspondence. It should be noted that the amount of data for producing an image (which is the amount represented by "Time range" in this drawing) requires one rotation of the gantry (to be accurate, one rotation plus the fan angle of the detector) or a half rotation thereof (to be accurate, a half rotation plus the fan angle of the detector) of data.

Helical cardiac imaging requires image reconstruction coherent at a specific time.

Figure 3:
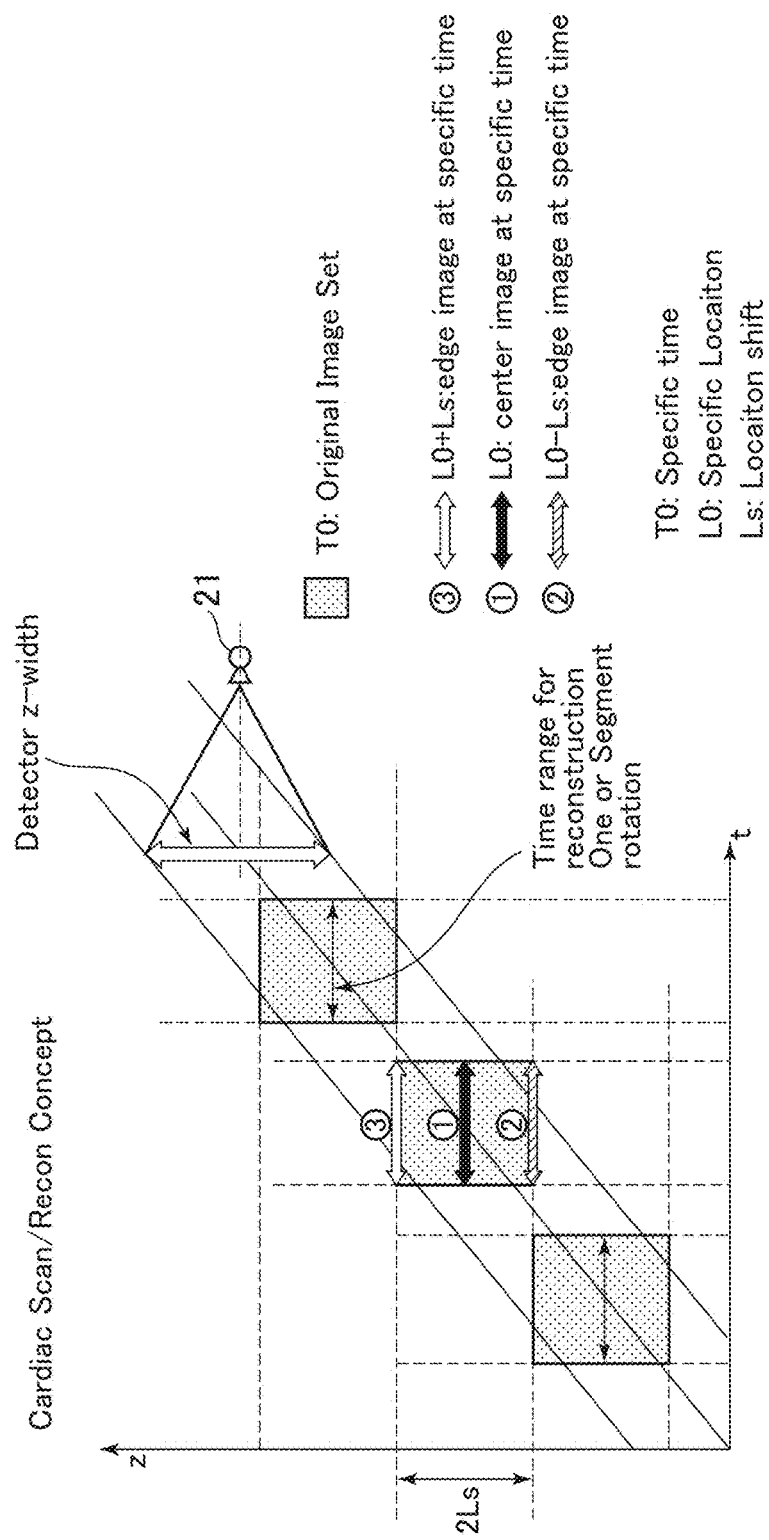
FIG. 3 A diagram showing a relationship between time and position during cardiac imaging according to a helical scan.

FIG. 3 shows a relationship between time t and position z during helical cardiac imaging. Because of helical imaging, the position of the X-ray detector changes with the lapse of time in one-to-one correspondence. However, data for use in image reconstruction at a specific time T0 has a margin for a location shift in the z-axis direction taking account of the z-width of the X-ray detector. Taking advantage of this fact, in cardiac image reconstruction, images at a plurality of positions may be produced at the specific time T0 to thereby create a set of cardiac images that are staying still at the specific time T0. This drawing shows a case in which images are produced at three mutually different positions L0, L0−Ls, L0+Ls, respectively, to create an image set consisting of these three images. Representing the positional width here as 2Ls (2×location shift), a central one of the set of the images is an image without a location shift (at a position of L0), while those lying at both edges in position are images with a location shift of Ls in positive and negative directions.

On the other hand, data for use in image reconstruction at a specific position sometimes has a margin for a time shift in a temporal axis direction taking account of the z-width of the X-ray detector. Taking advantage of this fact, local rapid motion of the intestinal tract or the like is detected by producing images at a plurality of times at a specific position, fragmenting each of these images, and comparing positionally corresponding local-region images with one another. In the case that any motion is detected, the fact is notified to the operator, or a scan protocol for re-imaging is automatically generated and presented to the operator. If possible, an image with the motion artifacts reduced is displayed.

Figure 4:
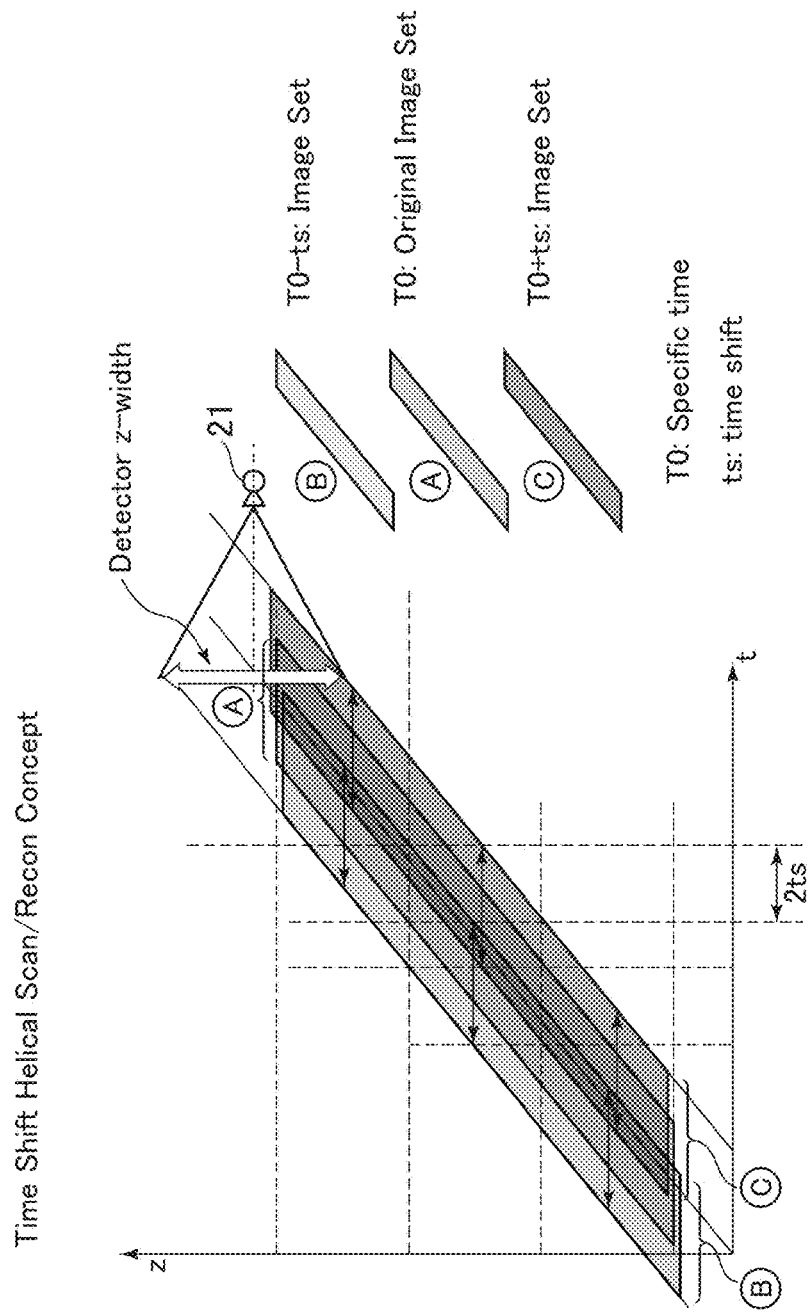
FIG. 4 A diagram showing the concept of making a time shift of a margin of scan data to reconstruct an image.

FIG. 4 shows the concept of making a time shift of the margin described above to reconstruct an image. As viewed from the relationship between time t and position z, a time shift is equivalent to a location shift. When placing an image produced at a specific time T0 with a location shift and an image produced in a different time zone without a location shift side by side at the same position, they may be considered as images with a time shift because they are images at the same position but the time of data acquisition is different. Hence, it is possible to make a time shift within the data coverage of the detector as shown. This drawing shows a case in which images are produced at three mutually different times T0, T0−ts, T0+ts, respectively, to create an image set consisting of the three images. Representing the time width here as 2ts (2×time shift), a central one of the set of the images is an image without a time shift (at a time of T0), while those lying at both edges in time are images with a time shift of is in positive and negative directions.

Figure 5:
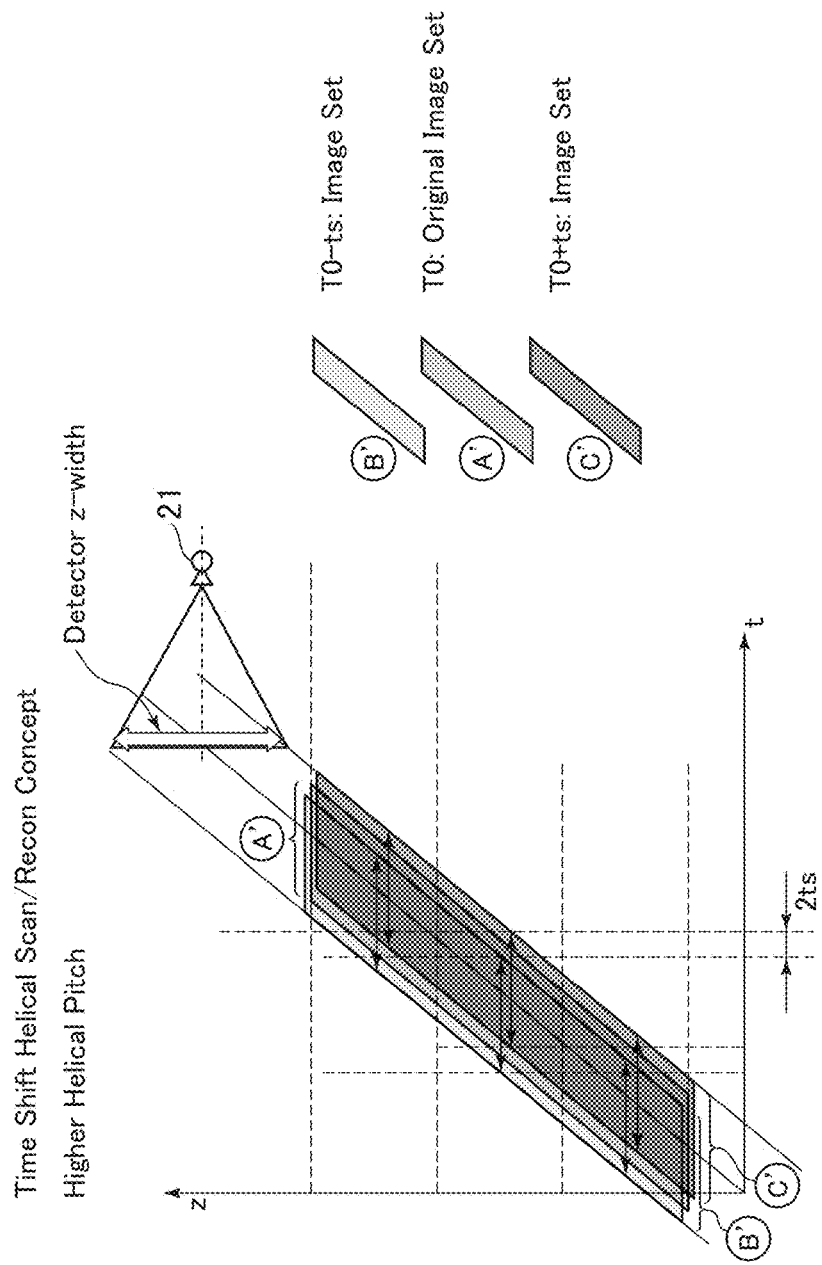
FIG. 5 A diagram showing the concept of making a time shift to reconstruct an image at a high helical pitch.

FIG. 5 shows the concept of reconstructing an image with a time shift for a high helical pitch. In the relationship between time t and position z, the margin described above is smaller for a higher helical pitch. This means that the amount 2ts available for the time shift is smaller. Similarly, as the rotation speed of the gantry becomes higher, the amount available for the time shift is reduced.

FIG. 6 shows roughly estimated amounts of the time width available for the time shift. The rough estimation is formed assuming that for each helical pitch HP, a margin corresponding to a pitch higher than that by one step is used for the time shift. The rough estimation is also formed taking account of the rotation speed V (sec/rot) of the gantry. Since motion of the intestinal tract or motion of bubbles and/or liquid within the intestinal tract is believed to be motion of the order of sub-seconds, i.e., several hundred milliseconds, it is possible to detect the motion of the intestinal tract or the like by selecting an appropriate helical pitch HP and rotation speed V.

Figure 7:
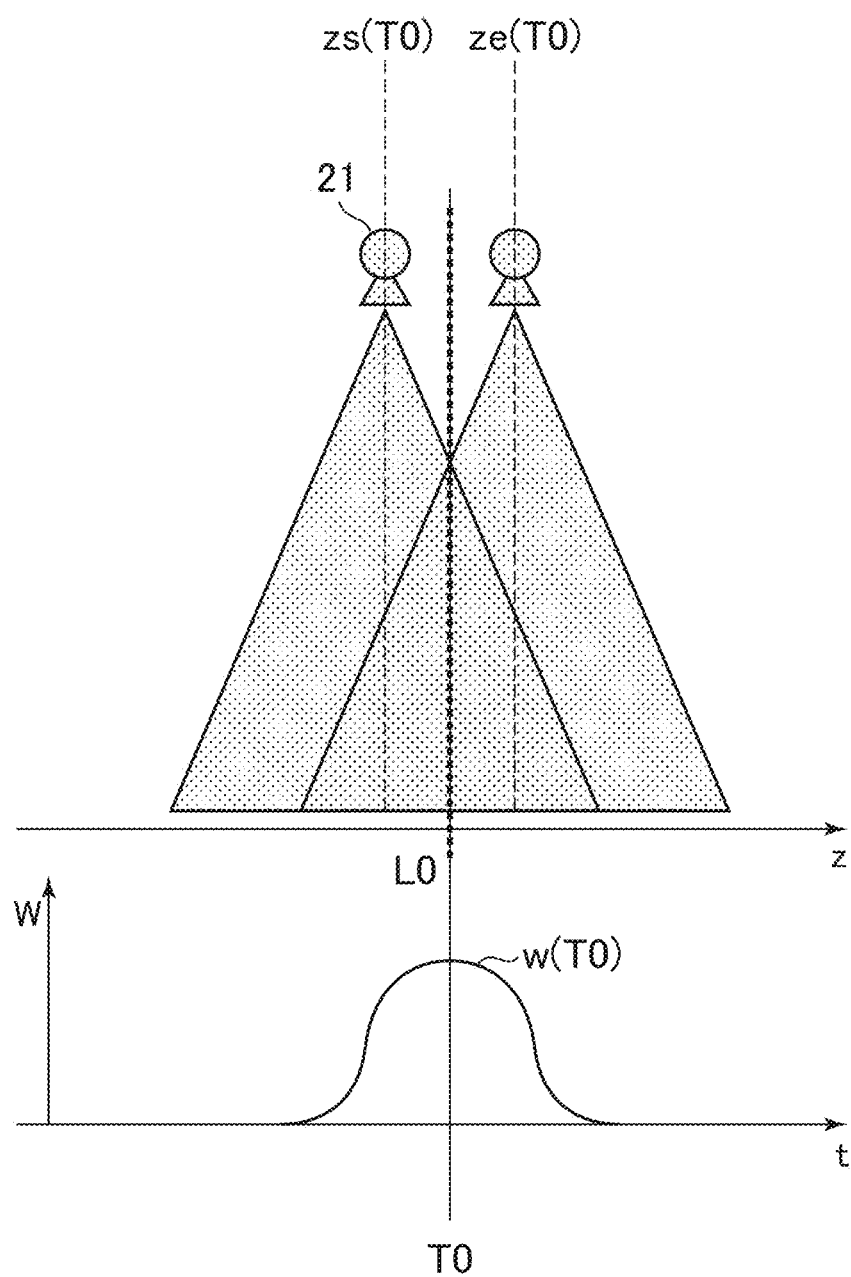
FIG. 7 A diagram showing a positional relationship between a general helical image and an X-ray detector, and a position-in-time of a weight function.

FIG. 7 shows an illustration of a positional relationship between a general helical image and the X-ray detector during data collection, and the position-in-time of a weight function. In this drawing, a physical position L0 indicated by a dashed line represents a slice position for which image reconstruction is applied, and it corresponds to a time T0. Moreover, two positions zs, ze of the X-ray detector represent the start- and end-point positions of a period of time for collection of the data for use in image reconstruction. The curve in the lower portion is a profile of a weight function w(T0) superposed over the data.

Figure 8:
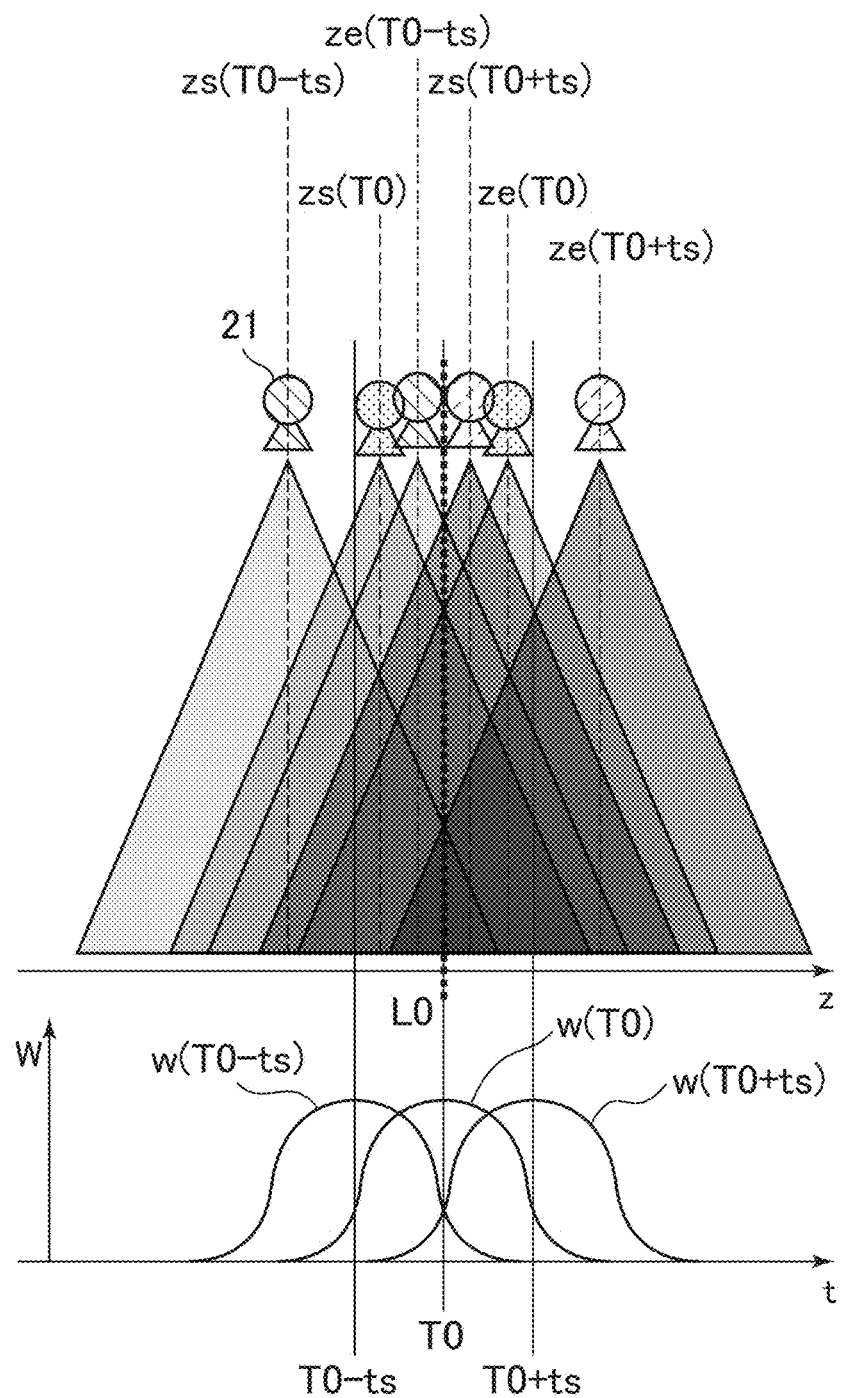
FIG. 8 A diagram showing a relationship between the position of a helical image with a time shift and the position of the X-ray detector during data collection, and the position-in-time of a weight function and a profile thereof.

FIG. 8 shows an illustration of a relationship between the position of a helical image with a time shift and the position of the X-ray detector during data collection, and the position-in-time of a weight function and a profile thereof.

This drawing represents a positional relationship of temporally backward and forward X-ray detector data regions and a shift in the position-in-time of the weight function, relative to the general case. In this drawing, a physical position L0 indicated by a dashed line represents a slice position for which image reconstruction is applied, and it corresponds to a time T0. Moreover, two position zs(T0), ze(T0) of the X-ray detector represent the start and end positions of collection of data for use in reconstruction of an image without a time shift. Likewise, the positions zs(T0−ts), ze(T0−ts) represent the start and end positions of collection of data for use in reconstruction of an image with a negative time shift. The positions zs(T0+ts), ze(T0+ts) represent the start and end positions of collection of data for use in reconstruction of an image with a positive time shift. The weight function w(T0) is a weight function superposed over the data for use in reconstruction of the image without a time shift. The weight function w(T0−ts) is a weight function superposed over the data for use in reconstruction of the image with a negative time shift. The weight function w(T0+ts) is a weight function superposed over the data for use in reconstruction of the image with a positive time shift.

When a time shift is applied, the physical position of the X-ray detector, more specifically, the center position of the region of data for use in reconstruction of an image, is coincident with the time of the image, but is not coincident with the position of the image. Moreover, the weight function w(T0) here is shifted in the temporal axis direction to be w(T0−ts) and w(T0+ts), although the shape of their profiles is not modified with the time shift in this drawing. However, in the case that a time shift is applied and more geometrically distant data is used, it is expected that the cone angle of the X-ray path for that data increases as well in view of geometry and accordingly artifacts increase. On the other hand, a conjugate beam having a rotation angle different by 180 degrees and lying oppositely may have corresponding data with a smaller cone angle.

Figure 9:
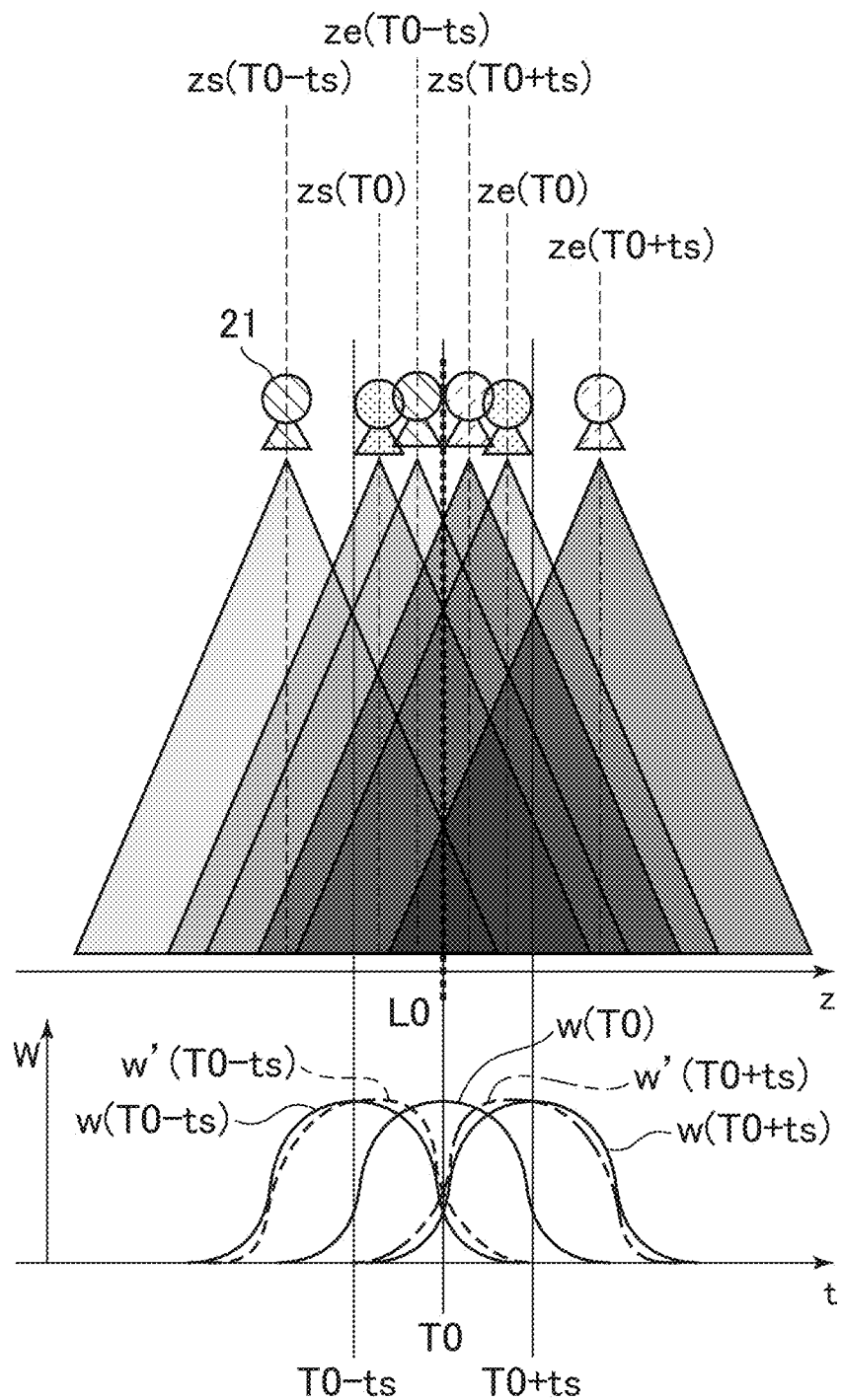
FIG. 9 A diagram showing an example of modification of the shape of the profile of the weight function when the time shift is applied.

FIG. 9 shows an example of modification of the shape of the profile of the weight function with a time shift. As shown, by modifying the shape of the weight function taking account of the cone angle of the X-ray path for data to be used according to the time shift ±ts as described above, the cone beam artifacts may be consequently more reduced. That is, a time T0±ts corresponding to a middle of the profile of the weight function with a time shift is coincident with the center of the period of time for collection of data for use in image reconstruction, and a weight function w'(T0±ts) formed by reducing the weight for a region having a larger cone angle of the X-ray path due to the time shift and increasing the weight for a region having a smaller cone angle of the X-ray path may be used to reduce cone beam artifacts more than the case with a simple time shift. It is thus essential to modify the shape of the weight function depending upon the time shift, in addition to the simple shift of the weight function. At that time, by modifying the shape of the profile of the weight function so that the half-width is as equal between the temporally backward and forward sides as possible, impact on the amount of time shift may be minimized.

FIG. 10 shows a case of an X-ray CT apparatus comprising a four-row detector in another example of modification of the shape of the weight function. The left side (FIG. 10A) of the drawing represents a case of a general helical scan without a time shift, wherein each row independently has a weight function, and the weight function is disposed according to the position in time at which an image position in each row is passed through. The right side (FIG. 10B) of the drawing represents modification of the shape of the weight function with a time shift. When a time shift is applied, it is necessary for row data lying farther from the image position to have a reduced proportion of contribution to an image. This is because data lying far from the image position has low reproducibility of information at the image position. In this case, again, it is essential to modify the shape of the weight function depending upon the time shift.

Images actually produced with a time shift, that is, three kinds of image in the example illustrated herein, are compared. Without any motion in the subject, the three kinds of image obtained should be almost the same. However, with intestinal motion or motion of bubbles and/or liquid within the intestinal tract, a difference occurs between at least two of the three kinds of image. The difference is believed to be often mainly caused from artifacts.

It is assumed here that motion in the subject including that which occurs in a partial organ, such as the intestinal tract, is detected. Accordingly, in detecting motion, the method proposed herein makes comparison among images produced with a time shift for local-region images, rather than for whole images, to search a partial region for movement. That is, each of a plurality of kinds of image produced with a time shift is fragmented into a respective plurality of local-region images, and a differential is determined among local-region images for each combination of the local-region images lying at the same position and at different times. Then, in the case that the differential exceeds a specified threshold level, it is decided that motion has possibly occurred. It should be noted that such a threshold level dynamically changed on a region-by-region, or body part-by-body part basis falls within expectations.

Thus, by comparing local-region images with one another for a plurality of kinds of image produced with a time shift, motion in a subject including partial motion, such as that of the intestinal tract, may be detected. Then, when any motion is detected, information on the fact is notified to the operator and consideration of re-imaging is recommended as needed.

At the same time, an imaging protocol for re-imaging may be automatically generated and presented to the operator. The imaging protocol may be one for performing re-imaging only on a portion in which motion is found, or one almost the same as that for previous imaging. In such cases, data obtained by re-imaging may be weighted and added to the data obtained in the previous imaging to reconstruct an image. For example, the weight on the data by re-imaging is increased for a portion in which motion is found while the weight for other portions is equalized for noise reduction. The weighted addition of data may be performed at the projection data stage or at the image stage after an image has been produced.

Moreover, it may be possible to provide an image with less artifacts than a conventional image by selectively displaying an image with relatively less artifacts from among such a plurality of kinds of image. When reduction of artifacts is insufficient, however, it may be considered to notify the fact to the operator as well.

Figure 11:
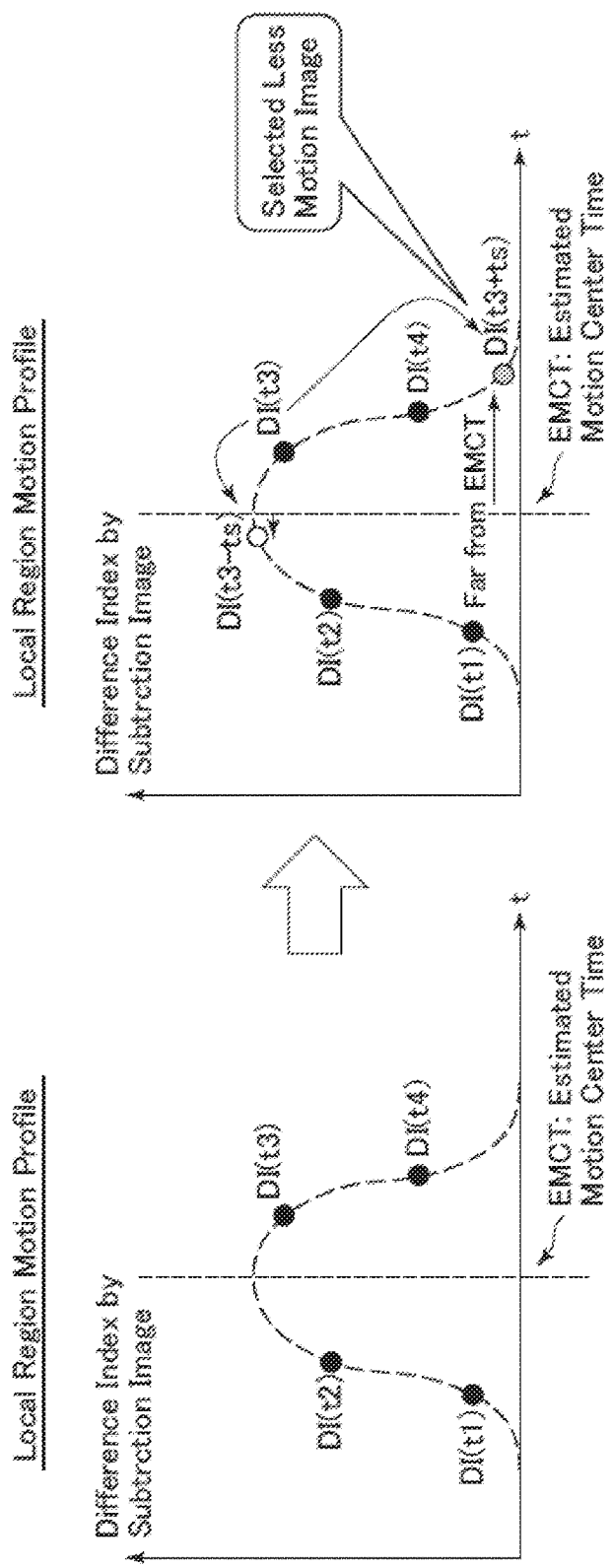
FIG. 11 A diagram for explaining a method of selecting an image with less artifacts.

FIG. 11 is a diagram for explaining a method of selecting an image with less artifacts.

When motion is detected in a local region, it may be considered that motion is detected similarly in image sets at times backward and forward. Therefore, the amount of motion in the image sets at respective times may be represented by a numeric value, and plotted at certain time intervals to thereby generate a motion profile. In this drawing, the amounts of motion DI(t1) to DI(t4) at times t1 to t4 are determined to make a plot. From a peak of such a profile, a center EMCT of the time in which motion occurs may be estimated. Based on the central time, an image with a time shift described above is produced, and a temporally distant image is selected. In this drawing, as an example, an image corresponding to a time t3+ts is selected from among those corresponding to times t3, t3−ts, t3+ts. This can provide an image with less motion.

It should be noted that the amount of motion represented by a numeric value may be estimated by, for example, accumulating a differential value between an image without a time shift and each of two kinds of image temporally shifted backward and forward, rather than between temporally shifted images, and estimating the amount based on the accumulated value.

Moreover, as the information to be notified to the operator, the presence/absence of motion may be notified, and in addition, the image with less motion selected as above may be presented along with the two other kinds of image, and the operator may be prompted to make a final selection.

Furthermore, an image with less motion may be automatically selected and registered, and along therewith, the result may be notified to the operator.

Figure 12:
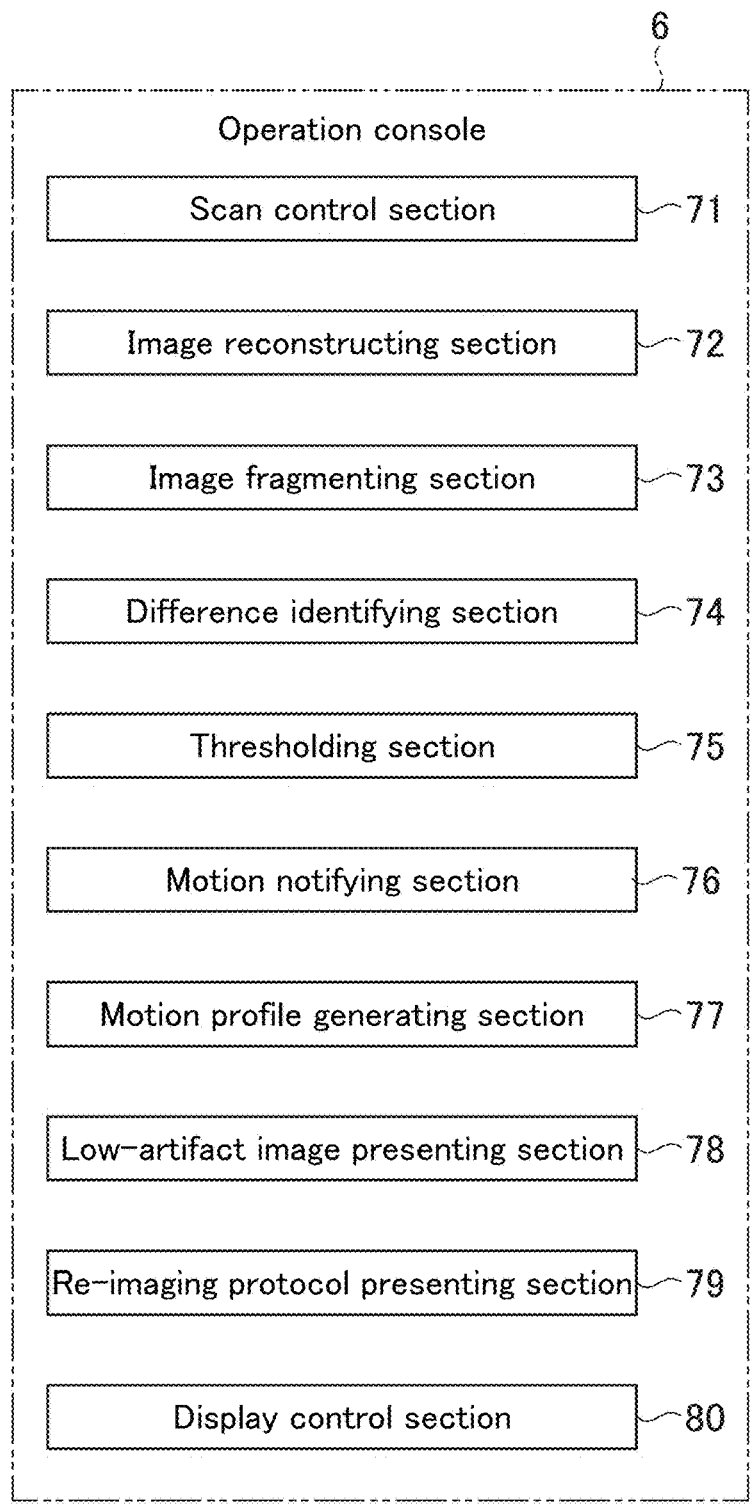
FIG. 12 A functional block diagram of an operation console in the X-ray CT apparatus in accordance with the present embodiment.

FIG. 12 is a functional block diagram of the operation console in the X-ray CT apparatus in accordance with the present embodiment.

The operation console 6 in the X-ray CT apparatus in accordance with the present embodiment has, as functional blocks for implementing the functions in accordance with the concept described above, a scan control section 71, an image reconstructing section 72, an image fragmenting section 73, a difference identifying section 74, a thresholding section 75, a motion notifying section 76, a motion profile generating section 77, a low-artifact image presenting section 78, a re-imaging protocol presenting section 79, and a display control section 80. These functional blocks are all designed/configured to implement the concept described above.

The scan control section 71 represents an example of the control means in the invention. The image reconstructing section 72 represents an example of the reconstructing means and second reconstructing means in the invention. The image fragmenting section 73 represents an example of the fragmenting means in the invention. The difference identifying section 74 represents an example of the difference identifying means in the invention. The thresholding section 75 and motion notifying section 76 represent an example of the notifying means in the invention. The motion profile generating section 77 represents an example of the acquiring means in the invention. The artifact-lowered image presenting section 78 represents an example of the image identifying means in the invention. The re-imaging protocol presenting section 79 represents an example of the presenting means in the invention.

The operation console 6 functions as these functional blocks by the computational processing apparatus 64 executing specified programs. The specified programs are stored in the storage device 63, or an externally connected storage device or medium 90, for example.

The scan control section 71 controls the gantry/table control section 30 so that a scan is performed in response to an operation by the operator. In the present example, a helical scan is performed as the scan.

The image reconstructing section 72 reconstructs an image based on data obtained by the scan. In the present example, data obtained by a helical scan is superposed with a plurality of kinds of weight function, and the resulting data is used to thereby reconstruct a multi-time image set consisting of a total of three kinds of image, including an image without a time shift, and two kinds of image temporally shifted backward and forward, at each slice position. The reconstruction of the temporally shifted images uses a weight function formed by reducing the weight on data in a region having a larger cone angle of the X-ray path and increasing the weight on data in a region having a smaller cone angle of the X-ray path, as described earlier.

The image fragmenting section 73 fragments, for a multi-time image set at each slice position, each image constituting the multi-time image set into a respective plurality of local-region images. In the present example, an image is horizontally and vertically divided into 10×10. A set of local-region images at the same position and at different times will be referred to herein as multi-time local-region image set.

The difference identifying section 74 identifies a difference among local-region images for each multi-time local-region image set at the same position and at different times. In the present example, a differential between the image without a time shift and the image temporally shifted backward is taken on a pixel-by-pixel basis to determine a total sum thereof. This is a first total sum. Likewise, a differential between the image without a time shift and the image temporally shifted forward is taken on a pixel-by-pixel basis to determine a total sum thereof. This is a second total sum. Then, a total differential value obtained by adding the first and second total sums together is determined as the difference described above.

The thresholding section 75 decides by a threshold whether or not the determined difference exceeds a specified level for each slice position and for each local region. In the present example, it decides whether or not the total differential value described above exceeds a specified threshold. In the case that an affirmative is given in this decision, it is decided that motion has occurred during imaging at that slice position and in that local region.

The motion notifying section 76 decides whether or not motion has occurred in any local region. In the case that motion is decided to have occurred, the fact is notified to the operator. Methods of notification may include, for example, one that displays a message on a screen of the display device 62, and one that outputs a chime sound or a voice from a speaker, which is not shown.

Still another method of notifying occurrence of motion that may be contemplated is one in which the thresholding section 75 determines the likelihood of occurrence of motion according to the amount or proportion of the excess of the aforementioned total differential value over the specified threshold, and the motion notifying section 76 displays the likelihood as a percentage.

The motion profile generating section 77 identifies, in the case that motion is decided to have occurred in any local region, a multi-time local-region image set corresponding to a plurality of times in a nearby volume of that local region. Then, the respective total differential values described above are determined as the amount of motion, and a relationship between the time and the amount of motion is plotted to generate a motion profile.

The low-artifact image presenting section 78 identifies a time when the amount of motion is small from the motion profile of the local region in which motion is found. Then, it identifies an image with a small amount of motion, i.e., image with less artifacts, from among the multi-time image set at the slice position in which the local region is included. The low-artifact image presenting section 78 presents the image with a small amount of motion from among the multi-time image set as a candidate for adoption, and along therewith, displays the other two kinds of image for comparison. In response to selection by the operator, an adopted image is determined.

The re-imaging protocol presenting section 79 creates, in the case that motion is decided to have occurred in any local region, an imaging protocol for imaging only the position of the slice including the local region in which motion has occurred and its nearby volume, and an imaging protocol according to similar conditions to those in previous imaging, and presents them.

The display control section 80 controls the display device 62 to display the several kinds of image and text on its screen.

Next, the flow of processing in the X-ray CT apparatus in accordance with the present embodiment will be described.

Figure 13:
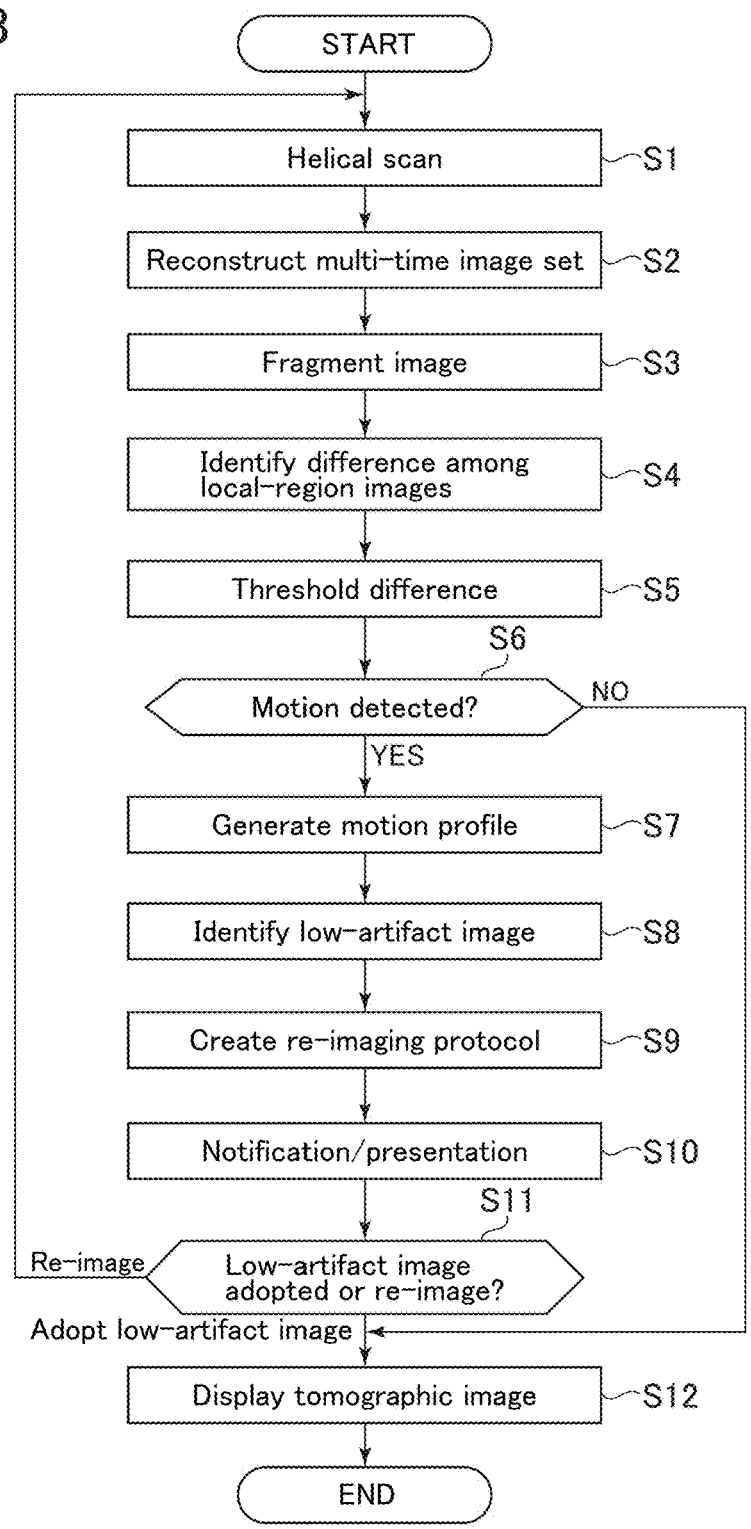
FIG. 13 A flow chart showing the flow of processing in the X-ray CT apparatus in accordance with the present embodiment.

FIG. 13 is a flow chart showing the flow of processing in the X-ray CT apparatus in accordance with the present embodiment. The steps in the flow are executed conforming to the concept described above.

At Step S1, a scan is performed. Specifically, the scan control section 71 controls the gantry/table control section 30 to perform a helical scan on a body part to be imaged 5h in the subject, which is an object to be imaged.

Figure 14:
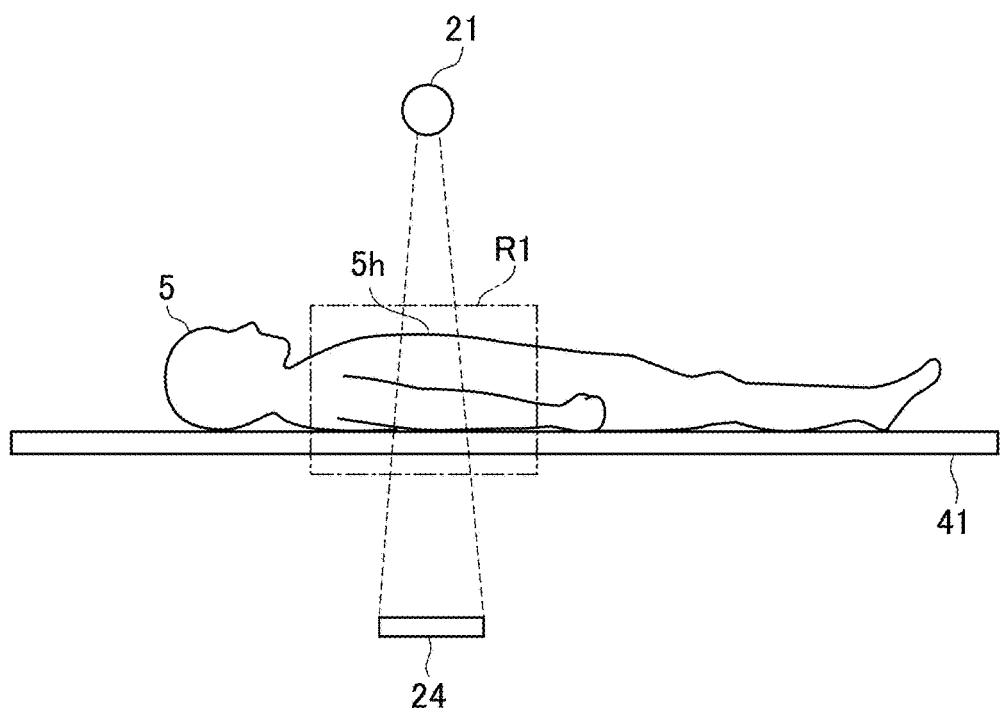
FIG. 14 A diagram showing a situation in which a body part to be imaged in a subject is scanned in the present embodiment.

FIG. 14 is a diagram schematically showing a situation in which the body part to be imaged 5h in the subject is scanned in the present embodiment. In the present example, a helical scan is performed on an imaging volume R1 including the body part to be imaged 5h in the subject 5 laid on the cradle 41, as shown in FIG. 14. The helical scan is achieved by emitting X-rays from the X-ray tube 21 at its X-ray focus onto the subject 5 while rotating the X-ray tube 21 and X-ray detector 24 around the subject 5, and at the same time, horizontally moving the cradle 41. The helical scan is performed assuming image reconstruction by what is generally called a full scan in which the view angle range is one rotation (360 degrees) of the gantry plus the fan angle α of the X-ray beam. Once the helical scan has been performed, X-ray detector data in a plurality of views along a helical axis are collected.

At Step S2, image reconstruction for a multi-time image set is performed. Specifically, the image reconstructing section 72 applies pre-processing to the X-ray detector data D in a plurality of views along the helical axis to provide projection data I in the plurality of views. The projection data I is then multiplied by the aforementioned weight function and back-projected to thereby reconstruct a multi-time image set consisting of an image without a time shift and two kinds of image temporally shifted backward and forward for each slice position.

At Step S3, fragmentation of an image is performed. Specifically, for a multi-time image set at each slice position, the image fragmenting section 73 fragments each image constituting the multi-time image set into a respective plurality of local-region images. In the present example, the size of an image is 512×512 pixels, and the image is horizontally and vertically divided into 10×10 local regions. A set of local-region images at the same position and at different times will be referred to herein as multi-time local-region image set.

At Step S4, a difference among local-region images is acquired. Specifically, the difference identifying section 75 identifies a difference among local-region images for each multi-time local-region image set at the same position and at different times. In the present example, a differential between the image without a time shift and the image temporally shifted backward is taken on a pixel-by-pixel basis to determine a total sum thereof. This is a first total sum. Likewise, a differential between the image without a time shift and the image temporally shifted forward is taken on a pixel-by-pixel basis to determine a total sum thereof.

This is a second total sum. Then, a feature quantity using the first and second total sums is determined as the difference described above. For example, a total differential value obtained by adding the first and second total sums together may be determined as the difference described above. It should be noted that the difference described above is not limited to the present example, and may be determined according to any one of various calculation formulae.

At Step S5, thresholding of the determined difference is performed. Specifically, the thresholding section 75 decides by a threshold whether or not the determined difference exceeds a specified level for each slice position and for each local region. In the present example, it decides whether or not the total differential value described above exceeds a specified threshold. In the case that an affirmative is given in this decision, it is decided that motion has occurred during imaging at that slice position and in that local region.

At Step S6, a decision is made as to whether or not motion in the subject is detected. Specifically, the motion notifying section 76 decides whether or not motion has occurred in any local region to thereby decide whether or not motion in the subject is detected. In the case that motion is detected, the flow goes to Step S7. In the case that no motion is detected, the flow goes to Step S12.

At Step S7, a motion profile is generated. Specifically, in the case that motion is decided to have occurred in any local region, the motion profile generating section 77 identifies a multi-time local-region image set corresponding to a plurality of times in a nearby volume of that local region. Then, the respective total differential values described above are determined as the amount of motion, and a relationship between the time and the amount of motion is plotted to generate a motion profile.

At Step S8, a low-artifact image is identified. Specifically, the low-artifact image presenting section 78 identifies a time with a small amount of motion from the motion profile of the local region in which motion is found. Then, it identifies an image with a smallest amount of motion, i.e., image with least artifacts, from among the multi-time image set at the position of the slice in which the local region is included. The image will be referred to herein as low-artifact image.

At Step S9, a protocol for re-imaging, i.e., imaging conditions for re-imaging, is created. Specifically, the re-imaging protocol presenting section 79 creates an imaging protocol for imaging only the position of the slice including the local region in which motion has occurred and a nearby volume, and an imaging protocol according to similar conditions to those in previous imaging.

At Step S10, notification of the fact that motion in the subject has occurred during imaging and presentation of a recommendation for handling are performed. Specifically, the motion notifying section 76 performs notification of the fact that motion has occurred during imaging. The low-artifact image presenting section 78 presents a low-artifact image with a small amount of motion as a candidate for adoption from among the multi-time image set at the position of the slice including the local region in which motion has occurred, and along therewith, displays two other kinds of image for comparison. Moreover, the re-imaging protocol presenting section 79 creates an imaging protocol for imaging only the position of the slice including the local region in which motion has occurred and a nearby volume, and an imaging protocol according to similar conditions to those in previous imaging, and presents them.

At Step S11, the operator selects one of the following options: adopting the low-artifact image that is the candidate for adoption; performing re-imaging using the imaging protocol for imaging only the portion in which motion has occurred; or performing re-imaging using the imaging protocol for similar imaging to previous imaging. In the case that re-imaging is selected, the flow goes back to Step S1 to perform re-imaging. In the case that adoption of the image that is the candidate for adoption is selected, the image is adopted and the flow goes to Step S12.

At Step S12, a tomographic image is displayed. Specifically, the display control section 80 controls the display device 62 to display the reconstructed tomographic image on its screen.

As described above, according to the present embodiment, a plurality of images at different times are reconstructed at each slice position based on data obtained by an X-ray-based helical scan, the images are each fragmented, a difference is determined among local regions, and in the case that the difference exceeds a specified level, motion is decided to be found during imaging in that local region; therefore, motion in a subject, particularly, local rapid motion such as motion of the intestinal tract, during X-ray tomographic imaging may be detected.

Moreover, according to the present embodiment, in the case that motion in the subject during imaging is detected, the fact is notified to the operator; therefore, the operator may be prompted to confirm that the reconstructed image is not disqualified. Furthermore, this enables the operator to efficiently realize occurrence of artifacts caused by motion in the subject, particularly, local rapid motion, during imaging that is easy to pass unnoticed.

According to the present embodiment, a weight function used to be superposed over data in reconstructing an image with a time shift is a weight function formed by reducing the weight for a region having a larger cone angle of an X-ray path and increasing the weight for a region having a smaller cone angle of the X-ray path; therefore, cone beam artifacts in a reconstructed image with a time shift may be reduced.

According to the present embodiment, in the case that motion is detected in a local region at a certain slice position, a motion profile near that local region is generated; therefore, a time with a smallest amount of motion within a time zone in which an image can be reconstructed at that slice position may be identified, and consequently, an image at a time with least motion artifacts may be identified and presented to the operator as a candidate for adoption.

According to the present embodiment, in the case that motion in a subject during imaging is detected, a protocol for re-imaging is automatically created and presented to the operator; therefore, smooth re-imaging is promoted.

According to the present embodiment, a plurality of images at an identical slice position and at different times are compared with one another and motion is detected based on the difference; therefore, implementation without an EKG (electrocardiographic) signal may be achieved. Moreover, even when cardiac imaging is to be performed, the technique of the present proposal may be extended to achieve cardiac imaging without an EKG signal.

While the present embodiment is an X-ray CT apparatus, the invention is also applicable to a tomographic imaging apparatus using radiation other than X-rays, for example, that using gamma rays.

In addition, a program for causing a computer to function as several means for performing control and/or processing in the X-ray CT apparatus described above and a recording medium in which such a program is stored each represent an exemplary embodiment of the invention as well.

The invention claimed is:

1. A radiation tomographic imaging method comprising:
utilizing a processor to execute:
a controlling step of controlling a data collection subsystem comprising a multi-slice detector to collect data of a plurality of views for a subject by performing a helical scan;
a first reconstructing step of reconstructing a plurality of tomographic images at an identical slice position and at different times using data obtained by applying weighting to the collected data of each view according to the slice position, the reconstruction being performed for a plurality of slice positions;
a fragmenting step of fragmenting each of the plurality of tomographic images at each of the plurality of slice positions into a respective plurality of local-region images; and
a difference identifying step of, for each combination of a plurality of local-region images at the same position and at different times, identifying a difference among local-region images in the combination;
wherein the first reconstructing step applies the weighting using a weight function that has a relatively small weight for a region with a relatively large cone angle of a radiation path and a relatively large weight for a region with a relatively small cone angle of the radiation path, and in which a middle of the weight function is coincident with a time of collection of data corresponding to the slice position for which image reconstruction is applied.

2. The radiation tomographic imaging method as recited in claim 1, comprising: a notifying step of, when a difference among local-region images in any the combination exceeds a specified level, notifying the fact.

3. The radiation tomographic imaging method as recited in claim 1, wherein: the first reconstructing step applies the weighting using a weight function tracing such a profile that a half width is equal between temporally backward and forward sides and a peak value is higher on a side closer to the time of collection of data corresponding to the slice position.

4. The radiation tomographic imaging method as recited in claim 1, comprising: an acquiring step of acquiring, when a difference among local-region images in any of the combinations exceeds a specified level, based on a difference among local-region images in the combination at the same position for two or more slice positions close to a specific slice position corresponding to the combination, a temporal change of an amount of motion of a body part at the specific slice position and at the same position.

5. The radiation tomographic imaging method as recited in claim 4, comprising: an image identifying step of identifying a tomographic image at a time when the amount of motion of the body part is relatively small based on the temporal change.

6. The radiation tomographic imaging method as recited in claim 1, comprising: a presenting step of presenting, when a difference among local-region images in any of the combinations exceeds a specified level, imaging conditions for re-scanning a range including the specific slice position corresponding to the combination.

7. The radiation tomographic imaging method as recited in claim 1, comprising: a second reconstructing step of reconstructing a tomographic image by adding data acquired by the re-scan together with data acquired before the re-scan.

8. The radiation tomographic imaging method as recited in claim 1, wherein: the fragmenting step performs fragmentation into images each having a width approximating to a diameter of an intestinal tract as the local-region images.

9. A radiation tomographic imaging apparatus comprising:
a processor configured to:
control a data collection subsystem comprising a multi-slice detector to collect data of a plurality of views for a subject by performing a helical scan;
reconstruct a plurality of tomographic images at an identical slice position and at different times using data obtained by applying weighting to the collected data of each view according to the slice position, the reconstruction being performed for a plurality of slice positions;
fragment each of the plurality of tomographic images at each of the plurality of slice positions into a respective plurality of local-region images; and
for each combination of a plurality of local-region images at the same position and at different times, identify a difference among local-region images in the combination;
wherein reconstructing the plurality of tomographic images comprises applying the weighting using a weight function that has a relatively small weight for a region with a relatively large cone angle of a radiation path and a relatively large weight for a region with a relatively small cone angle of the radiation path, and in which a middle of the weight function is coincident with a time of collection of data corresponding to the slice position for which image reconstruction is applied.

10. The radiation tomographic imaging apparatus as recited in claim 9, wherein the processor is further configured to, when a difference among local-region images in any of the combinations exceeds a specified level, generate a notification.

11. The radiation tomographic imaging apparatus as recited in claim 9, wherein reconstructing the plurality of tomographic images comprises applying the weighting using a weight function tracing such a profile that a half width is equal between temporally backward and forward sides and a peak value is higher on a side closer to the time of collection of data corresponding to the slice position for which image reconstruction is applied.

12. The radiation tomographic imaging apparatus as recited in claim 9, wherein the processor is further configured to acquire a temporal change of an amount of motion of a body part at the specific slice position and at the same position when a difference among local-region images in any of the combinations exceeds a specified level, based on a difference among local-region images in the combination at the same position for two or more slice positions close to a specific slice position corresponding to the combination.

13. The radiation tomographic imaging apparatus as recited in claim 12, wherein the processor is further configured to identify a tomographic image at a time when the amount of motion of the body part is relatively small based on the temporal change.

14. The radiation tomographic imaging apparatus as recited in claim 9, wherein the processor is further configured to present, when a difference among local-region images in any of the combinations exceeds a specified level, imaging conditions for re-scanning a range including the specific slice position corresponding to the combination.

15. The radiation tomographic imaging apparatus as recited in claim 9, wherein the processor is further configured to reconstruct an additional tomographic image by adding data acquired by the re-scan together with data acquired before the re-scan.

16. The radiation tomographic imaging apparatus as recited in claim 9, wherein fragmenting each of the plurality of tomographic images comprises performing fragmentation into images each having a width approximating to a diameter of an intestinal tract as the local-region images.

17. The radiation tomographic imaging apparatus as recited in claim 9, wherein:
- the local-region images in the combination comprise first, second and third local-region images at mutually different times, and
- the difference among local-region images in the combination is a feature quantity using a differential between the first and second local-region images, and a differential between the second and third local-region images.

\* \* \* \* \*